(12) United States Patent
Grutzendler et al.

(10) Patent No.: US 9,044,454 B2
(45) Date of Patent: Jun. 2, 2015

(54) REGULATION OF MICROVASCULATURE OCCLUSION

(75) Inventors: Jaime Grutzendler, Chicago, IL (US); Carson K. Lam, Chicago, IL (US); Taehwan Yoo, Ann Arbor, MI (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 747 days.

(21) Appl. No.: 13/045,265

(22) Filed: Mar. 10, 2011

(65) Prior Publication Data
US 2011/0223128 A1 Sep. 15, 2011

Related U.S. Application Data

(60) Provisional application No. 61/312,435, filed on Mar. 10, 2010.

(51) Int. Cl.
*A61K 31/38* (2006.01)
*A61K 31/575* (2006.01)
*A61K 31/745* (2006.01)

(52) U.S. Cl.
CPC ............... *A61K 31/38* (2013.01); *A61K 31/575* (2013.01); *A61K 31/745* (2013.01)

(58) Field of Classification Search
CPC .... A61K 31/38; A61K 31/575; A61K 31/745
See application file for complete search history.

(56) References Cited

U.S. PATENT DOCUMENTS

| | | | | |
|---|---|---|---|---|
| 6,548,667 | B2 * | 4/2003 | Park et al. | 544/62 |
| 7,001,617 | B2 * | 2/2006 | Burrell et al. | 424/618 |
| 2003/0211075 | A1 * | 11/2003 | Thorpe et al. | 424/85.1 |
| 2005/0287145 | A1 * | 12/2005 | Stewart et al. | 424/146.1 |
| 2006/0035833 | A1 * | 2/2006 | Hunter et al. | 514/12 |
| 2008/0057104 | A1 * | 3/2008 | Walker | 424/426 |

OTHER PUBLICATIONS

Sang et al., 2006, Matrix Metalloproteinase Inhibitors as prospective Agents for the Prevention and Treatment of Cardiovascular and Neoplastic Disease, Current Topics in Medicinal Chemistry, 6: 289-316.*
Palei et al., 2005, Hemodynamic benefits of matrix metalloproteinase-9 inhibition by doxycycline during experimental acute pulmonary embolism, Angiology, 56(5): 611-617.*
Ichihara et al., 1985, Transcatheter hepatic arterial embolization therapy using degradable polylactic acid microspheres, Gan To Kagaku Ryoho, 12(10): 1944-1945.*
Kruger et al., 2005, Antimetastatic Activity of a Novel Mechanism-Based Gelatinase Inhibitor, Cancer Res., 65(9): 3523-3526.*
Abbott et al., "Astrocyte-endothelial interactions at the blood-brain barrier," Nat Rev Neurosci, 7: 41-53 (2006).
Arvanitakis et al., "Diabetes mellitus and risk of Alzheimer disease and decline in cognitive function," Arch Neurol, 61: 661-666 (2004).
Busch et al., "Reperfusion after thrombolytic therapy of embolic stroke in the rat: magnetic resonance and biochemical imaging," J Cereb Blood Flow Metab, 18: 407-418 (1998).
Caplan & Hennerici, "Impaired clearance of emboli (washout) is an important link between hypoperfusion, embolism, and ischemic stroke," Arch Neurol, 55: 1475-1482 (1998).
Carman & Springer, "A transmigratory cup in leukocyte diapedesis both through individual vascular endothelial cells and between them," J Cell Biol, 167: 377-388 (2004).
Collen, "On the regulation and control of fibrinolysis. Edward Kowalski Memorial Lecture," Thromb Haemost, 43: 77-89 (1980).
Davies, "Flow-mediated endothelial mechanotransduction," Physiol Rev, 75: 519-560 (1995).
Dejana, "Endothelial cell-cell junctions: happy together," Nat Rev Mol Cell Biol, 5: 261-270 (2004).
Dermietzel et al., Blood-brain barriers: from ontogeny to artificial interfaces. Weiheim; [Chichester]: Wiley-VCH (2006), only TOC; 32 pages.
Engelhardt & Wolburg, "Mini-review: Transendothelial migration of leukocytes: through the front door or around the side of the house?," Eur J Immunol, 34: 2955-2963 (2004).
Farkas & Luiten, "Cerebral microvascular pathology in aging and Alzheimer's disease," Prog Neurobiol, 64: 575-611 (2001).
Gleerup & Winther, "The effect of ageing on platelet function and fibrinolytic activity," Angiology, 46: 715-718 (1995).
Iadecola & Gorelick, "Converging pathogenic mechanisms in vascular and neurodegenerative dementia," Stroke, 34: 335-337 (2003).
Iadecola, "Neurovascular regulation in the normal brain and in Alzheimer's disease," Nat Rev Neurosci, 5: 347-360 (2004).
Kai et al., "Peripheral blood levels of matrix metalloproteases-2 and -9 are elevated in patients with acute coronary syndromes," J Am Coll Cardiol, 32: 368-372 (1998).
Kamei et al., "Endothelial tubes assemble from intracellular vacuoles in vivo," Nature, 442: 453-456 (2006).
Levin & Del Zoppo, "Localization of tissue plasminogen activator in the endothelium of a limited number of vessels," Am J Pathol, 144: 855-861 (1994).
Lo et al., "tPA and proteolysis in the neurovascular unit," Stroke, 35: 354-356 (2004).
Mark & Davis, "Cerebral microvascular changes in permeability and tight junctions induced by hypoxia-reoxygenation," Am J Physiol Heart Circ Physiol, 282:H1485-1494 (2002).
Markus et al., "Asymptomatic cerebral embolic signals in symptomatic and asymptomatic carotid artery disease," Brain, 118(Pt. 4): 1005-1011 (1995).
Muller, "Leukocyte-endothelial-cell interactions in leukocyte transmigration and the inflammatory response," Trends Immunol, 24: 327-334 (2003).
Nishimura et al., "Targeted insult to subsurface cortical blood vessels using ultrashort laser pulses: three models of stroke," Nat Methods, 3: 99-108 (2006).

(Continued)

*Primary Examiner* — Amber D Steele
(74) *Attorney, Agent, or Firm* — Casimir Jones, S.C.

(57) ABSTRACT

The present invention provides compositions and methods to regulate embolic occlusion of the microvasculature. In particular, the present invention inhibits extravasation of emboli from microvasculature resulting in increased occlusion (e.g., by administering a MMP 2/9 inhibitor locally to a subject).

7 Claims, 3 Drawing Sheets

(56) References Cited

OTHER PUBLICATIONS

Peppiatt et al., "Bidirectional control of CNS capillary diameter by pericytes," Nature, 443: 700-704 (2006).

Powers et al., "Cerebral blood flow and cerebral metabolic rate of oxygen requirements for cerebral function and viability in humans," J Cereb Blood Flow Metab, 5: 600-608 (1985).

Pugsley et al., "The impact of microemboli during cardiopulmonary bypass on neuropsychological functioning," Stroke, 25: 1393-1399 (1994).

Purandare et al., "Asymptomatic spontaneous cerebral emboli predict cognitive and functional decline in dementia," Biol Psychiatry, 62: 339-344 (2007).

Rapp et al., "Atheroemboli to the brain: size threshold for causing acute neuronal cell death," J Vasc Surg, 32: 68-76 (2000).

Rieckmann & Engelhardt, "Building up the blood-brain barrier," Nat Med, 9: 828-829 (2003).

Siebler et al., "Cerebral microembolism in symptomatic and asymptomatic high-grade internal carotid artery stenosis," Neurology, 44: 615-618 (1994).

Stratman et al., "Endothelial cell lumen and vascular guidance tunnel formation requires MT1-MMP-dependent proteolysis in 3-dimensional collagen matrices," Blood, 114: 237-247 (2009).

Vermeer et al., "Silent brain infarcts and the risk of dementia and cognitive decline," N Engl J Med, 348: 1215-1222 (2003).

Wagner & Chen, "Transcapillary transport of solute by the endothelial vesicular system: evidence from thin serial section analysis," Microvasc Res, 42: 139-150 (1991).

Yang et al., "Matrix metalloproteinase-mediated disruption of tight junction proteins in cerebral vessels is reversed by synthetic matrix metalloproteinase inhibitor in focal ischemia in rat," J Cereb Blood Flow Metab, 27: 697-709 (2007).

Yong et al., "Metalloproteinases in biology and pathology of the nervous system.," Nat Rev Neurosci, 2: 502-511 (2001).

Zhao et al., "Role of matrix metalloproteinases in delayed cortical responses after stroke," Nat Med, 12: 441-445 (2006).

Zlokovic, The Blood-Brain Barrier in Health and Chronic Neurodegenerative Disorder, Neuron, 57:178-201 (2008).

\* cited by examiner

REGULATION OF MICROVASCULATURE OCCLUSION

This Application claims priority to U.S. Provisional Application No.: 61/312,435, filed Mar. 10, 2010, herein incorporated by reference in its entirety.

STATEMENT REGARDING FEDERALLY SPONSORED RESEARCH OR DEVELOPMENT

This invention was made with government support under Grant No. 5R01AG027855-02 awarded by the National Institutes of Health. The government has certain rights in the invention.

FIELD OF THE INVENTION

The present invention provides compositions and methods to regulate embolic occlusion of the microvasculature. In particular, the present invention inhibits extravasation of emboli from microvasculature resulting in enhanced occlusion (e.g., by administering a MMP 2/9 inhibitor locally to a subject).

BACKGROUND

Emboli form, for example, as a result of the presence of foreign matter in the bloodstream or can arise spontaneously. Vascular emboli are a major single causative agent for multiple human pathologies, and are a leading cause of disability and death. Clots or thrombi that become dislodged from the point of origin are termed emboli. Such particulate matter may originate from a blood clot occurring in the heart, a foreign body, or may be derived from body tissues. For example, atherosclerosis (fatty or calcified deposits in blood vessel walls), may cause emboli to form. Moreover, clots can form on the luminal surface of the atheroma, as platelets, fibrin, red blood cells and activated clotting factors may adhere to the surface of blood vessels to form a clot. Blood clots or thrombi may also form in the veins of subjects who are immobilized, particularly in the legs of bedridden or other immobilized patients. These clots may then travel in the bloodstream, potentially to the arteries of the lungs, leading to a common, often-deadly disease called 'pulmonary embolus'. Thrombus formation, and subsequent movement to form an embolus, may occur in the heart or other parts of the arterial system, causing acute reduction of blood supply and hence ischemia. The ischemic damage often leads to tissue necrosis of organs such as the kidneys, retina, bowel, heart, limbs, brain or other organs, or even death.

Cerebral function and viability are dependent on uninterrupted blood flow through the microvasculature for adequate oxygen and glucose delivery (Powers et al., 1985). Thus, robust mechanisms to ensure microvascular patency must have evolved. The fibrinolytic system is a highly regulated mechanism that ensures the degradation of fibrin clots occluding cerebral blood vessels (Collen, 1980) including terminal arterioles and capillaries (Levin and del Zoppo, 1994). However, microvessels, because of their small diameter and relative low flow velocity, may be prone to occlusion by clots as well as detritus not susceptible to fibrinolysis such as fragments of atheromatous plaques (Rapp et al., 2000, herein incorporated by reference in its entirety).

SUMMARY OF THE INVENTION

In some embodiments, the present invention comprises a method of regulating recanalization of microvessels comprising regulating embolus extravasation. In some embodiments, regulating recanalization of microvessels comprises regulating recanalization of microvessels within a specific tissue or tissue region. In some embodiments, regulating embolus extravasation comprises inhibiting recanalization of microvessels by inhibiting embolus extravasation. In some embodiments, inhibiting embolus extravasation inhibits the removal of blockages from the microvasculature. In some embodiments, blockages comprise cell matter, thrombus, cholesterol, atherosclerotic plaque, fat droplets, air bubbles, gas bubbles, pus, coagulants produced by bacteria, body tissues, foreign bodies, amniotic embolus, or microspheres. In some embodiments, inhibiting embolus extravasation results in decreased blood flow through the microvasculature. In some embodiments, inhibiting embolus extravasation in a specific tissue or tissue region damages the tissue or tissue region. In some embodiments, the tissue or tissue region comprises diseased tissue or a tumor. In some embodiments, inhibiting embolus extravasation induces apoptosis with the tissue or tissue region.

In some embodiments, the present invention provides a method of inducing cell death within a tissue comprising inhibiting recanalization of the microvasculature within the tissue. In some embodiments, the tissue comprises a specific tissue type or region of tissue. In some embodiments, the tissue comprises a tumor or diseased tissue. In some embodiments, inhibiting recanalization of the microvasculature comprises inhibiting embolus extravasation. In some embodiments, inhibiting embolus extravasation inhibits the removal of blockages from the microvasculature. In some embodiments, blockages comprise cell matter, thrombus, cholesterol, atherosclerotic plaque, fat droplets, air bubbles, gas bubbles, pus, coagulants produced by bacteria, body tissues, foreign bodies, amniotic embolus, or microspheres. In some embodiments, the inhibiting embolus extravasation results in decreased blood flow through the microvasculature. In some embodiments, inhibiting recanalization comprises administering an inhibitory composition to the tissue. In some embodiments, the present invention further comprises administering emboli to the microvasculature with a tissue. In some embodiments, the emboli comprise synthetically produced emboli. In some embodiments, the emboli comprise microspheres. In some embodiments, the present invention further comprises administering a therapeutic to the tissue. In some embodiments, the decreased blood flow through the microvasculature slows the removal of the therapeutic from the tissue. In some embodiments, the therapeutic is a chemotherapeutic. In some embodiments, the emboli comprise the therapeutic. In certain embodiments, the methods further comprise administering a MMP 2/9 inhibitor to a subject (e.g., locally to a subject, such as at a site of a tumor).

In some embodiments, the present invention provides a method of concentrating a therapeutic in a region of tissue comprising: (a) inhibiting recanalization of the microvasculature within the tissue; (b) administering emboli into the microvasculature with the tissue, wherein the emboli form blockages in the microvasculature which cannot be efficiently removed; and (c) administering a therapeutic to the tissue, wherein the tissue is not efficiently removed from the tissue because the blood flow is restricted by blockage of the microvasculature. In some embodiments, the therapeutic and the emboli are administered concurrently. In some embodiments, the emboli comprise the therapeutic. In some embodiments, inhibition of recanalization is reversible or temporary.

In some embodiments, the concentration of therapeutic results in more efficient treatment of said tissue.

BRIEF DESCRIPTION OF THE FIGURES

The following drawings form part of the present specification and are included to further illustrate aspects of the present invention. The drawings highlight exemplary embodiments of the present invention, but should not be viewed as limiting the scope of the invention. The invention may be better understood by reference to the drawings in combination with the detailed description of the specific embodiments presented herein.

DETAILED DESCRIPTION OF THE INVENTION

Figure 1:
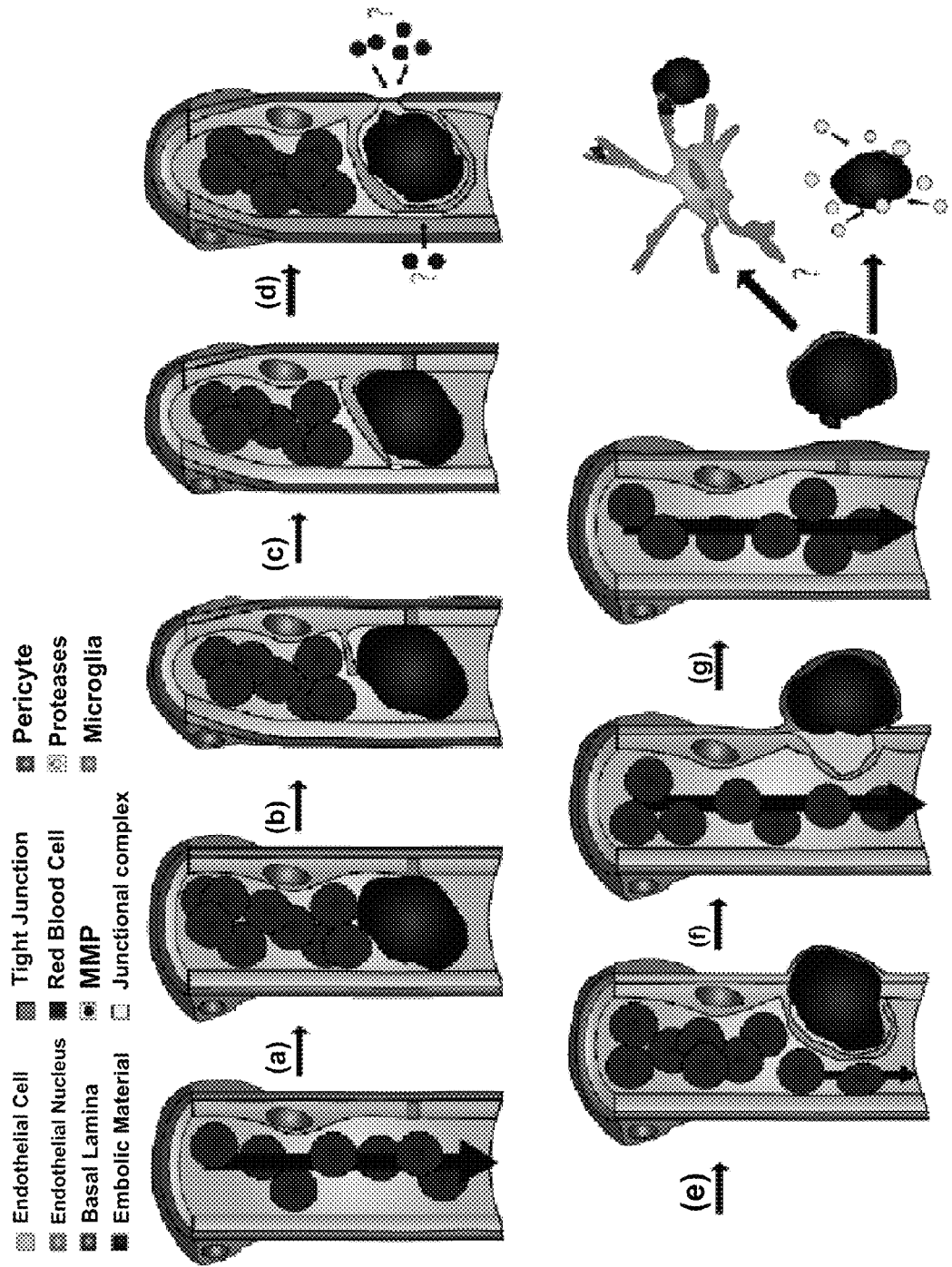
FIG. 1 shows a schematic of an exemplary mechanism of embolus extravasation: (a) If hemodynamic forces and the fibrinolytic system fail to clear occluded microvessels within the first few hours post occlusion, their efficiency is very low for clearing vessels thereafter. The following alternative mechanisms are then triggered: (b) Gradual extension of a membrane projection derived from the adjacent endothelium around the embolus: (c) The new membrane projection completely envelops the adjacent embolus. Cell-cell adhesion complexes are observed between the new membrane and the preexisting adjacent endothelium. These junctions aid in the guidance of the new membrane during the envelopment process and assure that no plasma flow occurs at this stage. (d) Matrix metalloproteases induce tight junction and basal lamina disruption leading to the formation of an endothelial opening for embolus translocation into the perivascular parenchyma. MMPs may be involved in disruption of adhesive complexes between the new membrane and adjacent endothelium leading to their dissociation. Pericytes may induce vessel constriction, which combined with hemodynamic forces aids in extruding the embolus. (e) Once the embolus is completely enveloped by the endothelial membrane, a narrow lumen is formed through which plasma and in larger arterioles some cells can flow. (f) Emboli are then extruded through the endothelial opening and the new endothelial membrane realigns to form a new vessel wall. Normal blood flow is re-established. (g) Extravasated embolic material is gradually degraded. Mechanisms of degradation include microglia phagocytosis as well extravascular proteolysis of fibrin clots. Prompt embolus extravasation ultimately leads to recovery of normal blood flow and prevents microvessel damage.

The present invention provides compositions and methods to regulate embolic occlusion of the microvasculature. In particular, the present invention inhibits extravasation of emboli from microvasculature resulting in increased occlusion.

Microvascular occlusion by emboli occurs spontaneously throughout life and is common in a variety of disease processes. Although small vessel occlusions usually produce little acute symptomatology, their cumulative effect likely leads to organ dysfunction. This is especially relevant in the brain where micro-occlusions may eventually lead to cognitive impairment. The established view has been that microvascular emboli are normally cleared by hemodynamic forces and the fibrinolytic system. However, the present invention establishes an alternative cellular mechanism that effectively removes emboli composed of virtually any substance, including those not susceptible to fibrinolysis such as atheromatous cholesterol fragments, from the microvasculature (e.g. cerebral microvasculature). Clearance occurs by a previously unknown process of microvascular plasticity involving the engulfment of entire emboli by endothelial membrane projections and their subsequent translocation into the perivascular parenchyma leading to rapid reestablishment of blood flow and vessel sparing. In aging mice, the rate of embolus extravasation is severely delayed. Pathways involved in mechanotransduction, vascular plasticity, cytoskeletal dynamics, remodeling of endothelial junctions and extracellular matrix play critical roles and are affected in aging. In some embodiments, alterations in these molecular pathways significantly alter the efficiency of embolus extravasation, impacting the viability of occluded microvessels and surrounding tissue. Experiments were performed during development of embodiments of the present invention to determine the molecular control mechanisms of the extravasation process.

In some embodiments, the present invention provides compositions and methods to regulate, alter, modify, and/or affect embolic occlusion of the microvasculature. In some embodiments, the present invention provides compositions and methods to regulate, alter, modify, and/or affect extravasation of emboli from microvasculature. In some embodiments, the present invention inhibits extravasation of emboli from microvasculature resulting in increased occlusion. In some embodiments, the present invention enhances extravasation of emboli from microvasculature resulting in decreased occlusion. In some embodiments, the present invention increases occlusion (e.g. embolic occlusion) of the microvasculature. In some embodiments, the present invention reduces occlusion (e.g. embolic occlusion) of the microvasculature.

In some embodiments, debris and or emboli comprise cell matter, thrombus (blood clot), cholesterol, atherosclerotic plaque, fat droplets, air bubbles, gas bubbles, pus or coagulants produced by bacteria, body tissues, foreign bodies (e.g. talc), amniotic embolus, etc. In some embodiments, debris and/or emboli comprise solid, liquid, and/or gaseous phase. In some embodiments, debris form anterograde, retrograde, and/or paradoxical embolus.

In some embodiments emboli are formed, travel through, and/or are dislodged from arteries or veins including, for example, the ascending aorta, right coronary artery, left coronary artery, anterior interventricular, circumflex, left marginal arteries, posterolateral artery, intermedius, arch of aorta, brachiocephalic artery, common carotid artery, internal carotid artery, external carotid artery, subclavian artery, vertebral artery, internal thoracic artery, thyrocervical trunk, deep cervical artery, dorsal scapular artery, brachial artery, thoracic aorta, abdominal aorta, inferior phrenic, celiac, superior mesenteric, middle suprarenal, renal, anterior and posterior, interlobar artery, gonadal, lumbar, inferior mesenteric, median sacral, common iliac, common iliac arteries, internal iliac artery, anterior division, obturator artery, superior vesical artery, vaginal artery (females), inferior vesical artery (males), middle rectal artery, internal pudendal artery, inferior gluteal artery, uterine artery (females), deferential artery (males), (obliterated) umbilical artery, posterior division, iliolumbar artery, lateral sacral artery, superior gluteal artery, external iliac artery, inferior epigastric artery, deep circumflex iliac artery, femoral artery, superficial epigastric artery, superficial circumflex iliac artery, superficial external pudendal artery, deep external pudendal artery, deep femoral artery, descending genicular artery, popliteal artery, anterior tibial artery, posterior tibial artery, sural artery, medial superior genicular artery, lateral superior genicular artery, middle genicular artery, inferior lateral, inferior medial genicular artery, external jugular vein, right innominate vein, superior vena cava, azygos vein, cephalic vein, basilic vein, renal vein, common iliac vein, femoral vein, popliteal vein, posterior tibial vein, anterior tibial vein, dorsal venous arch, small saphenous vein, great saphenous vein, hypogastric vein, ulnar vein, radial vein, inferior vena cava, brachial vein, axillary veiun, subclavian vein, left innominate vein, internal jugular vein, etc.

In some embodiments, debris and or emboli partially and/or completely occlude one or more regions of the microvasculature. In some embodiments, debris and/or emboli travel from larger blood vessels into the microvasculature. In some embodiments, debris and or emboli break off from and/or travel through major vasculature, but partially and/or completely occlude one or more regions of the microvasculature. In some embodiments, debris and/or emboli travel from body tissues into the microvasculature. In some embodiments, debris and/or emboli which are able to flow freely through larger vasculature (e.g. veins and arteries) can become caught or lodged in the microvasculature resulting in partial and/or complete occlusion of one or more regions of the microvasculature. In some embodiments, microvasculature comprises one or more of arterioles, capillaries, metarterioles, sinusoids, venules, and/or microcirculation. In some embodiments, emboli and/or debris partially or entirely occlude regions of the vasculature (e.g. microvasculature). In some embodiments, emboli and/or debris partially or entirely restrict blood flow through regions of the vasculature (e.g. microvasculature).

In some embodiments, the fibrinolytic system and/or other well known systems of debris and/or emboli removal are not capable of removing certain debris and/or emboli (e.g. non-fibrin based debris and/or emboli). In some embodiments, the fibrinolytic system and/or other well known systems of debris and/or emboli removal are not capable of removing debris and/or emboli from regions of the microvasculature.

In some embodiments, the present invention provides a mechanism for removal of debris and/or emboli form the vasculature (e.g. microvasculature). In some embodiments, debris and/or emboli are removed from the microvasculature. In some embodiments, occlusions are removed from the vasculature (e.g. microvasculature). In some embodiments, non-fibrin-containing debris and/or emboli are removed and/or cleared from the vasculature (e.g. microvasculature). In some embodiments, fibrin-containing and/or non-fibrin-containing debris and/or emboli are cleared from the vasculature (e.g. microvasculature). In some embodiments, the present invention provides a mechanism for removal and/or clearing of debris and/or emboli (e.g. non-fibrin debris and/or emboli) from the vasculature (e.g. microvasculature). In some embodiments, the present invention provides clearing of non-fibrin debris from the microvasculature. In some embodiments, occlusions are cleared from the microvasculature. In some embodiments, non-fibrin occlusions are cleared from the vasculature (e.g. microvasculature).

In some embodiments, the present invention provides a regulated mechanism for the removal and/or clearing or debris, emboli, and/or occlusions from the vasculature (e.g. microvasculature). In some embodiments, occlusions, debris, and/or emboli are translocated to the extravascular space. In some embodiments, fibrin-containing and/or non-fibrin-containing debris, emboli, and/or occlusions are extravasated. In some embodiments, extravasation of debris, emboli, and/or occlusions is the result of one or more regulated pathways. In some embodiments, extravasation and/or extravasation pathways are induced by occlusion of the vasculature (e.g. microvasculature). In some embodiments, extravasated debris and/or emboli (e.g. fibrin containing and/or non-fibrin-containing) are dispersed and/or degraded. In some embodiments, debris, emboli, clots, and or occlusions are phagocytosed. In some embodiments, extravasated occlusions are phagocytosed by phagocytes (e.g. monocytes, macrophages, neutrophils, sinusoidal cells, lining cells, osteoclasts, histiocytes, dendric cells, microglial cells, resident Langerhans cells, mast cells, Kupffer cells, lymphocytes, NK cells, LGL cells, epithelial cells, fibroblasts, erythrocytes, etc.). In some embodiments, extravasated occlusions are phagocytosed by perivascular phagocytes. In some embodiments, extravasated occlusions are phagocytosed by extravascular phagocytes. In some embodiments, extravasated occlusions are phagocytosed by microglial cells (e.g. perivascular microglial cells). In some embodiments, extravasated occlusions are phagocytosed by perivascular microglial cells. In some embodiments, multiple cell types play roles in the processes of extravasation and/or phagocytosis. In some embodiments, various cell types (e.g. perivascular cells) interact with debris, emboli, and/or occlusions during the extravasation, phagocytosis, degradation, and/or dispersion processes. In some embodiments, astrocytes interact (e.g. end feet of astrocytes enwrap extravasated debris) with extravasated material. In some embodiments, enzymes (e.g. proteolytic enzymes) play a role in the degradation and/or dispersion of extravasated material. In some embodiment, enzymes are secreted by cells (e.g. perivascular cells, extravascular cells, etc.) to facilitate degradation of extravasated material. In some embodiments, extravasated material is broken down into fragments and dispersed. In some embodiments, extravasation allows removal of fragments without further degradation. In some embodiments, occlusions and/or emboli are degraded and/or fragmented prior to extravasation. In some embodiments occlusions and/or emboli are extravasated with reduction to fragments. In some embodiments, phagocytosis is initiated following extravasation. In some embodiments, phagocytosis is initiated concurrently with extravasation. In some embodiments, phagocytosis is initiated prior to extravasation.

In some embodiments, material forming blockages and/or occlusions (e.g. emboli, debris, etc.) may be of any diameter (e.g. >0.1 µm, >1 µm, 1-5 µm, 1-10 µm, 5-20 µm, 10-50 µm, 1-100 µm, 50-250 µm, 100-1000 µm, <1 mm, <5 mm, and all diameters therein). In some embodiments, different pathways and mechanisms are utilized for extravasation, phagocytosis, degradation, and/or dispersion of blockages and emboli of different sizes. In some embodiments, similar or the same pathways and mechanisms are utilized for extravasation, phagocytosis, degradation, and/or dispersion of blockages and emboli of different sizes. In some embodiments, blockages and occlusion comprise cell matter, thrombus (blood clot), cholesterol, atherosclerotic plaque, fat droplets, air bubbles, gas bubbles, pus or coagulants produced by bacteria, body tissues, foreign bodies (e.g. talc), amniotic embolus, and/or any combination thereof. In some embodiments, different pathways and mechanisms are utilized for extravasation, phagocytosis, degradation, and/or dispersion of blockages and emboli comprising different component materials (e.g. fibrin, cell matter, air bubbles, pus, etc.). In some embodiments, similar or the same pathways and/or mechanisms are utilized for extravasation, phagocytosis, degradation, and/or dispersion of blockages and emboli comprising different component materials (e.g. fibrin, cell matter, air bubbles, pus, etc.).

In some embodiments, blood vessel (e.g. vasculature, microvaculature) constriction occurs prior to or concurrently with extravasation. In some embodiments, constriction of blood vessels occurs in the region of the occlusion. In some embodiments, blood vessel constriction plays a role in extravasation of emboli and/or occlusions. In some embodiments, blood vessel constriction occurs as a consequence of extravasation, phagocytosis, degradation, and/or dispersion of blockages and emboli. In some embodiments, blood vessel(s) remain constricted following extravasation. In some embodiments, blood vessel(s) become unconstricted following extravasation. In some embodiments, pericytes and/or smooth muscle cells mediate constriction during the extravasation process. In some embodiments, pericytes are recruited to the region adjacent to occlusions and/or emboli to be extravasated. In some embodiments, pericytes become hypertrophied around occluded microvasculature. In some embodiments, vascular constriction mediates fragmenting of occluding emboli. In some embodiments, vascular constriction mediates extruding debris and/or emboli through the endothelium. In some embodiments, vascular constriction reduces potential leakage of blood components through openings in the endothelium before, during, and after extravasation.

In some embodiments, opening of the vasculature for extravasation is a tightly controlled process. In some embodiments, opening of the vasculature for extravasation is short-lived. In some embodiments, a breach in the blood brain barrier (BBB) provides a paracellular pathway for occlusion and/or fragment extravasation. In some embodiments, extravasation comprises re-patterning, movement, and/or recruiting of various cellular components and/or proteins (e.g. tight junction, basement membrane, Zonula Occuludens-1, Occuludin, Collagen IV, etc.) to the site of extravasation. In some embodiments, extravasation is mediated by and/or results in rearrangement of endothelial cytoskeletal proteins. In some embodiments, one or more proteases mediate embolus degradation and/or extravasation. In some embodiments, one or more proteases (e.g. matrix metalloproteinases (e.g. MMP 2/9) are involved in degrading vasculature, endothelium, and/or other tissues to mediate extravasation. In some embodiments, vascular occlusion (e.g. microvascular occlusion) induces activity of proteases (e.g. matrix metalloproteinases (e.g. MMP 2/9) is adjacent cellular structures. In some embodiments, proteins, enhancer molecules, repression molecules, proteinases, regulatory proteins, and other proteins and regulatory molecules mediate induction and regulation of the steps of the extravasation process (e.g. fragmentation, degradation, extravasation, dispersion, constriction, etc.). In some embodiments, the extravasation process involves the stages of vascular mechanosensing, hypoxia sensing, cytoskeletal dynamics and regulation of vascular plasticity, endothelial junction and extracellular matrix remodeling. In some embodiments, proteins, enhancer molecules, repression molecules, proteinases, regulatory proteins, and other proteins and regulatory molecules mediate induction and regulation of the stages of the extravasation process. In some embodiments, the present invention provides inhibiting, inducing, repressing, and/or enhancing molecules (e.g. proteins (e.g. proteases (e.g. matrix metalloproteinases (e.g. MMP 2/9) involved in steps of the extravasation process (e.g. fragmentation, degradation, extravasation, dispersion, constriction, etc.)

In some embodiments, the present provides compositions and methods for regulation of the pathways and/or mechanisms involved in extravasation, phagocytosis, degradation, and/or dispersion of blockages and emboli from the vasculature (e.g. microvasculature). In some embodiments, the present invention provides compositions and methods for targeting regulators, inhibitors, and/or activators of one or more processes, mechanisms, and/or steps involved in extravasation of blockages from the microvasculature. In some embodiments, compositions and methods target (e g inhibit and or activate) regulators of the actin cytoskeleton (e.g. Rho GTPases), for example, through the delivery of small molecule inhibitors (e.g. ToxinB, NSC23766, C3 exotoxin, etc.) or activators. In some embodiment, compositions and methods target (e g inhibit and or activate) proteins which are involved in migration of, or interactions between, actin and myosin, for example, myosin light chain kinase (MLCK), the delivery of small molecule inhibitors (e.g. ML-7 and ML-9). In some embodiments, compositions and methods target (e g inhibit and or activate) ion channels, for example, members of the transient receptor potential (TRP) family (e.g. receptor potential vanilloid-4 (TRPV4) receptor). In some embodiments, compositions and methods target (e g inhibit and or activate) hypoxia-inducible factor 1, α-subunit (HIF 1 α) and/or vascular endothelial growth factor (VEGF). In some embodiments, compositions and methods target (e.g. inhibit and or activate) adherens junction proteins, such as VE-cadherin, or proteins concentrated at endothelial cell-cell junctions, such asPECAM-1 and integrins. In some embodiments, compositions and methods target (e g inhibit and or activate) proteolytic enzymes, such as matrix metalloproteinases (e.g. MMP2/9). In some embodiments, compositions and methods target (e.g. inhibit and or activate) molecular markers of synapse, glial, neurons and blood vessels as well as cell death markers (synaptophysin, cytochrome-C, MAP-2, IBA-1, GFAP, S-100, CD-31, Caspase-3, etc.).

In some embodiments, the present invention provides compositions and methods for inhibition of the pathways and/or mechanisms involved in extravasation, phagocytosis, degradation, and/or dispersion of blockages and emboli from the microvasculature. In some embodiments, the present invention provides compositions and methods which enhance occlusion of the microvasculature. In some embodiments, enhancing occlusion of the microvasculature mediates regional embolization (e.g. tumor embolization, organ embolization, tissue embolization, etc.). In some embodiments, the extravasation of occlusions and/or emboli is inhibited to promote regional embolization (e.g. tumor embolization, organ embolization, tissue embolization, etc.). In some embodiments, embolization of a region of tissue promote and/or initiates apoptosis and/or necrosis of that region of tissue.

In some embodiments, the present invention provides compositions and methods for non-surgical tissue destruction. In some embodiments, the present invention provides compositions and methods to inhibit extravasation, phagocytosis, degradation, and/or dispersion of blockages and emboli from microvasculature in order to damage, destroy, and/or kill the tissue surrounding the microvasculature. In some embodiments, inhibition one or more steps of the emboli extravasation pathway provides regional targeting of tissue for destruction (e.g. cancer therapy). In some embodiments, extravasation of emboli is inhibited in tumor tissue, diseased tissue, tissue to be removed. In some embodiments, a tissue (e.g. tumor, diseased tissue, etc.) is targeted for destruction by inhibition of extravasation of emboli form the microvasculature within that tissue. In some embodiments, inhibition of extravasation within the microvasculature of a tissue results in blockage of the microvasculature, poor blood flow within the tissue, and death (e.g. apoptosis, necrosis, etc) of the tissue surrounding the microvasculature. In some embodiments, inhibition of extravasation within the microvasculature of a tissue (e.g. tumor, diseased tissue, etc.) results in apoptosis of the tissue.

In some embodiments, inhibition of extravasation is accompanied by one or more mechanisms for promoting embolization. In some embodiments, emboli of a specific size are deployed into the microvasculature (e.g. microvasculature of a particular region and/or tissue (e.g. a tumor) prior to, following, or concurrent with inhibition of extravasation of the same microvasculature. In some embodiments, deployment of emboli in conjunction with inhibition of extravasation enhances the destructive effect on the region of tissue. In some embodiments, the size of the emboli deployed is selected based on the size of the microvasculature to be blocked. In some embodiments, emboli of any suitable diameter may be used (e.g. >0.1 µm, >1 µm, 1-5 µm, 1-10 µm, 5-20 µm, 10-50 µm, 1-100 µm, 50-250 µm, 100-1000 µm, <1 mm, <5 mm, and all diameters therein). In some embodiments, emboli to be deployed may be synthetic (e.g. polymer, nanoparticle, liposomes, etc.) or naturally occurring (e.g. cell debris (e.g. purified cell debris), fat, cholesterol, etc.). In some embodiments, emboli to be deployed comprise microspheres comprising one or more materials (e.g. chitosan, agarose, or gelatin, etc.). In some embodiments, microspheres are configured to occlude microvessels. In some embodiments, microspheres are configured to occlude microvessels while carrying and releasing specific substances (e.g. inhibitors of extravasation, therapeutics, etc.). In some embodiments, microspheres are fluorescently tagged (e.g. with quantum dots) to allow visualization of the microspheres in the microvasculature (e.g. blocking the microvasculature, being extravasated, being dispersed, etc.) In some embodiments, differently labeled microspheres carrying unique cargo (e g inhibitors of extravasation, therapeutics, etc.) various cargo concentrations can be simultaneously infused into the microvasculature and monitored based on different labels with distinct emissions.

In some embodiments, the present invention provides compositions and methods for concentrating therapeutics in a desired region or tissue. In some embodiments, inhibition of extravasation is accompanied by release of therapeutic (e.g. chemotherapy, antibiotic, any pharmaceutical, etc.) into the vasculature, and the decreased flow caused by the lack of removal of blockages concentrates the therapeutic in the region of interest. In some embodiments, therapeutics are administered and extravasation is temporarily inhibited to provide concentration of the therapeutic in a given region or tissue (e.g. tumor tissue) for a specified time period without causing prolonged damage to the tissue. In some embodiments, inhibition of extravasation is accompanied by release of emboli to block the microvasculature and a desired therapeutic to be concentrated.

In some embodiments, the present invention provides temporary inhibition of extravasation. In some embodiments, blockage of the microvasculature induced by the present invention is temporary. In some embodiments, the present invention provides reversible inhibition of extravasation. In some embodiments, blockage of the microvasculature induced by the present invention is reversible.

EXPERIMENTAL

The following section provides exemplary embodiments of the present invention, and should not be considered to be limiting of its scope with regard to alternative embodiments that are not explicitly described herein.

Example 1

Compositions and Methods

To induce cerebral embolization fluorescently conjugated fibrin clots, cholesterol emboli (8-20 µm in diameter) or polystyrene microspheres (10 or 15 µm in diameter) were infused through the mouse internal carotid artery. Emboli were imaged in fixed tissues by confocal microscopy after vessel labeling by I.V. injection of FITC-lycopersicom esculentum, thioflavin-S or immunolabeled with anti-PECAM-1, collagen IV or ZO-1 antibodies. Emboli were also imaged overtime in vivo by transcranial two-photon microscopy (TPM) in mice expressing GFP in endothelial cells (Tie2-GFP) or wild type mice injected with thioflavin-S I.V. Blood flow velocity was recorded by line scan TPM imaging to verify microvascular occlusion and reestablishment of flow. Transmission electron microscopy was obtained after injection of fibrin emboli conjugated to electron dense colloidal carbon. Quantification of extravasation efficiency was performed from confocal images in fixed brain slices and in a subset of experiments from in vivo TPM time-lapse images. Matrix metalloprotease 2/9 (MMP2/9) activity was measured in areas adjacent to emboli using fluorescent in situ zymography methods. SB-3CT was administered to selectively inhibit MMP2/9 activity and determine the role of MMPs in the extravasation process. Perivascular hypoxia was detected by administration and immunohistochemical detection of hypoxyprobe. Dendritic spine density was quantified in confocal image stacks of fixed brain slices from mice expressing YFP in a subset of pyramidal neurons. Immunohistochemistry for synaptophysin was used for comparison of synapse-puncta between adult and aged mice. Immunohistochemistry with NG2 and IBA1 antibodies was used to study microglia and pericytes around areas of occlusion.

Animals: CB6F1 mice (Jackson Labs) were used for young-aged comparison studies. Tie2-GFP mice (Jackson Labs) were used for in vivo TPM imaging of microvessels. Thy1-YFPH mice (B6.Cg-Tg (Thy1-YFP)16Jrs/J; Jackson labs) were used to visualize neuronal processes and quantify dendritic spines. Mice expressing GFP under the CX3CR1 chemokine receptor promoter were used for in vivo imaging of microglia (B6.129P(Cg)-Ptprc$^a$ Cx3cr1$^{tm1Litt}$/LittJ; Jackson labs). Mice expressing eGFP under control of the chicken beta actin promoter (ACTB-eGFP; Jackson labs) were used to visualize cells flowing in vessels. Other experiments used CD1 mice. Studies were conducted in mice between 3-5 months old with the exception of aging studies which used 22 month-old mice.

Preparation of emboli: Heterologous fibrin-rich clots were generated by collecting blood from the left ventricle of mice with the same genetic background as the experimental ones. Mouse thrombin (10 µl of 1000 NIH units/mg; Sigma) was added to blood immediately after extraction and incubated at room temperature for 1 hour. Clots were rinsed with ddH$_2$O to induce cell lysis. To facilitate clot production and minimize the unnecessary sacrifice of mice, experiments requiring a larger number of animals were done with clots generated directly from fibrinogen (Sigma #F8630; 0.6 g/ml in 1×PBS). For either method, fibrin clots were fragmented by sonication and fluorescently conjugated by incubation for 4 hours with Texas Red-X succimydyl ester (1 mg/ml in ethanol; Invitrogen). Labeled clot fragments were washed with 70% EtOH and filtered through sieves (8-20 µm pore size; Biodesign) and re-suspended in 1× PBS at predetermined concentrations to achieve sparse microvascular occlusion. For detection with transmission electron microscopy, clots were conjugated to colloidal carbon (Higgins, waterproof india ink, passed through a 200 nm. filter)) or polysterene nanoparticles (Duke scientific, 48 nm.) by mixing the fibrinogen solution (500 µl) with the carbon or nanoparticle suspension prior to thrombin administration for clot generation. Cholesterol emboli were generated by melting cholesterol crystals (100 mg; Sigma) at 150° C. and adding Texas Red-X succimydyl ester to label them fluorescently. The solution was crystallized at room temperature and sonicated in 1× PBS. Cholesterol fragments were filtered through sieves (8-20 µm pore size; Biodesign) and resuspended in 1× PBS at predetermined concentrations to achieve sparse embolization. Microsphere emboli were prepared by diluting red fluorescent polystyrene microspheres (10 or 15 µm) (1.25×10$^4$ microspheres/ml; EZ-Trac, IMT/Stason) in 1× PBS at predetermined concentrations to achieve sparse embolization.

Embolization Surgery: Mice were anesthetized by either intraperitoneal injection of ketamine/xylazine (120 mg/mL/ 10 mg/mL) or inhaled isoflurane. A ventral midline incision was made in the neck to gain access to the left common carotid artery (CCA). The CCA was separated from surrounding connective tissue and blood flow was interrupted by means of retracting sutures. The left external carotid was clamped with temporary ligating sutures to divert emboli into the cerebral circulation via the left internal carotid artery. A small incision was made in the CCA with fine microsurgical scissors and a custom made catheter attached to a Hamilton syringe filled with 200 µl of solution containing emboli at the desired concentrations was inserted into the CCA. All types of emboli were infused over a ~2 minute period. The catheter was removed and the incision was resealed with cyanoacrylate glue (Scotch). Ligating sutures were removed and CCA patency was confirmed by observation of adequate blood filling and CCA pulsations. The surgical wound was sutured and mice were carefully monitored post-operatively.

In vivo two photon imaging: Anesthetized mice previously infused with emboli were injected through the tail vein with ~100 µl of Thioflavin-S (1% in 0.5% PBS; Sigma), Rhodamine-B dextran (1% in 1× PBS; Invitrogen) or Clear Blue dye (Risk reactor) to label the cerebral vasculature. A midline scalp incision was made and an imaging window was created above the somatosensory cortex by thinning a ~700 µm diameter skull area with a high-speed drill (Fine Science Tools) as previously described[9] followed by skull immobilization by attachment to a stainless steel plate. Before two-photon imaging, the precise location of emboli was mapped by taking a digital image of the surface microvasculature and respective emboli under fluorescence microscopy. A two photon microscope (Prairie technologies) was used for in vivo imaging. The Ti-sapphire laser (Coherent Inc.) was tuned to 890 nm for simultaneous imaging of microvessels, microglia and emboli. Images were taken using a water immersion objective (Olympus 40×, 0.8 N.A.) at a z-step of 1 µm and zoom of 1-4×. Blood flow velocity was recorded in individual cortical microvessels using line scan imaging of flowing blood cells and fluorescent intravascular dye (Kleinfeld et al. Proc Natl Acad Sci USA 95, 15741-6 (1998), herein incorporated by reference in its entiorety). After imaging, the skull plate was removed and the scalp incision was closed with 6-0 nylon sutures (Ethicon). The animal was placed back into its cage and monitored until the next imaging time point.

Quantification of Emboli Retention, Washout and Extravasation:

Early washout (embolus retention): Fibrin or cholesterol emboli were infused through the internal carotid artery. Two hour post embolization mice were sacrificed and postfixed with 4% PFA without cardiac perfusion to avoid perfusion-induced embolus washout. Brain vibratome sections (100 µm) were obtained and imaged with fluorescence microscopy. The total number of emboli in the brain was estimated by counting number of emboli within a sample of representative slices per animal and extrapolating the total number of emboli in the brain taking into account the total number of slices in the forebrain. Data are reported as absolute number of emboli counted.

Delayed washout: mice were injected with fibrin or cholesterol emboli and processed in the same way as described above. Mice were sacrificed at various time points ranging from 2 hours to 6 days. The absolute number of remaining emboli was calculated at each time point and subtracted from the results obtained from the number of emboli remaining at 2 hours postembolization. Washout was plotted as the percentage change overtime of emboli remaining in the brain.

Extravasation: Mice were embolized with fibrin, cholesterol or polystyrene emboli. Prior to sacrifice, cerebral vasculature was labeled by I.V. injection of fluorescently-conjugated lectin lycopersicom esculentum (100 µl, 1 mg/ml; Vector laboratories). Brain slices (50 µm) were obtained with a vibratome and imaged with confocal microscope to quantify extravasation. Emboli were classified by whether they remained within the lumen or were outside of it. Extravasation rate was calculated as the number of extravasation events divided by the total number of clots counted in all brain slices:

$$\text{Embolic extravasation efficiency} = \frac{\sum \text{extravasated emboli}}{\sum \text{all emboli}}$$

Quantification of extravasation efficiency using microspheres eliminates the potential bias caused by extravascular degradation of clots, fibrinolysis or washout of clots and the ambiguity encountered when categorizing partially extravasated clots into extravasated or non-extravasated categories. Furthermore, microsphere size and shape are very uniform allowing accurate comparisons between aged and young mice or pharmacologically treated mice.

Measurement of extravasation in MMP 2/9 inhibitor injected mice: Mice embolized with either fibrin clots or microspheres were injected daily (intraperitoneally) with selective MMP 2/9 inhibitor SB-3CT (2 mg/ml in 20% DMSO/ddH$_2$O; Biomol). Microsphere-embolized mice were treated daily with saline or SB-3CT at 2, 10, and 20 mg/kg/ day or acutely with 40 mg/kg. Clot-embolized mice were given saline or SB-3CT at 20 mg/kg/day. Mice were sacrificed at 4 days post-embolization for clots and 14 days post-embolization for microspheres because of their different time courses of extravasation.

In situ zymography: Brains were harvested at various intervals postembolization with clots or microspheres and rapidly frozen without fixation. Tissues were cryosectioned (20 μm thick) and embedded in fluorescein conjugated DQ gelatin from pig skin (15 mg/ml, Invitrogen) for 15 minutes at 4° C. and then for 5 hours at 25° C. Tissues were then rinsed with PBS and fixed with 4% paraformaldehyde followed by fluorescence quantification.

Immunohistochemical labeling: Brain tissue was extracted after perfusion and post-fixed with 4% paraformaldehyde in 1× PBS, cryosectioned, and blocked with 3% normal goat serum/0.1% triton-X100. Incubation with primary antibodies was carried out overnight at 4° C. The primary antibodies used were: smooth muscle actin (Abcam), collagen IV (Abcam), BrdU (AbD Serotec), NG2 chondroitin (Chemicon), Hypoxyprobe (Chemicon), occludin (Invitrogen), ZO-1 (Invitrogen), synaptophysin (Chemicon), CD31(PECAM-1) (BD Pharmigen), and IBA1 (Wako). For hypoxia detection, Hypoxyprobe (60 mg/kg; Chemicon) was injected intraperitoneally into embolized mice 2 hours before sacrifice. To detect cell proliferation, BrdU (40 mg/kg; Sigma-Aldrich) was injected intraperitoneally every 24 hours post-embolization until sacrifice.

Fluorescence quantification: ZO-1, NG2, hypoxyprobe and in situ zymography fluorescence was quantified from confocal images of brain slices from embolized mice. A region of interest (ROI) of fixed size was placed centered around the embolus. The average grey scale intensity within this ROI was calculated with NIH Image J software and normalized to fluorescence intensity in multiple control areas measured in adjacent non-occluded microvessels of equal diameter present within the same confocal optical plane. This normalization procedure controls for inter-animal immunolabeling variability and fluorescence intensity due to different imaging depths within a confocal stack. The data is computed as a ratio between the ROI and control areas within the same optical plane, this allows comparison of the ratios rather than absolute fluorescence values between different samples.

Dendritic spine quantification: Thy1-YFPH mice were embolized with 15 μm microspheres, and sacrificed at different time points post-embolization (5 min, day 1, day 7, and day 42). Prior to sacrifice, the intravascular dye thioflavin-S was injected. Confocal imaging of YFP-expressing dendrites in the immediate vicinity of occluded vessels was obtained. Dendrites were segmented into 3 equal portions: area 1 was the intersection between the dendrite and the downstream unperfused portion of the vessel (as determined by reduced intravascular fluorescence); area 2 and area 3 were, respectively, the distal and proximal segments of the dendrite to area 1 and served as internal controls. Spine density was quantified from confocal stacks and normalized as follows:

$$\text{normalized spine density} = \frac{\text{area 1 density}}{\frac{\text{area 2 density} + \text{area 3 density}}{2}}$$

Electron Microscopy: Mice were perfused with a 4% paraformaldeyde and 1% glutaraldehyde solution 7-12 days post-embolization with 10 μm microspheres or 4-8 days postembolization with fibrin clots conjugated to Texas red-X ester (Invitrogen) as well as 48 nm nanoparticles or colloidal carbon (as described above). Coronal brain vibratome (Leica) sections (35 μm) were generated. Diaminobenzidine (DAB; Sigma; 0.06% DAB in a 5% 0.05M Tris buffer at a pH 7.6) was used to photoconvert the fluorescent clots (irradiated at 480 nm wavelength with a 120V mercury lamp). The photoconverted dark clots were located under a dissecting microscope and microdissected with the tip of a 30 gauge needle into ~200 μm diameter pieces containing the occluded vessel. The tissue was processed for electron microscopy using standard methods. Tissues were immersed in 1% osmium tetroxide for 1 hour at room temperature then dehydrated in an increasing concentration gradient of ethanol. Once fully dehydrated, tissue was transitioned in propylene oxide before being put into EMBED-812 (Election Microscopy Sciences) overnight. The tissues were placed into an oven at 60° C. for 24 hours for polymerization. Embedded tissues were then placed on pre-made epoxy blocks with a drop of resin and placed back in the oven for an additional 24 hours. 70 nm sections were cut on a microtome (Leica), placed on copper grids and allowed to dry for 24 hours at room temperature. Contrast enhancement was achieved by placing the grids on a 4% uranyl acetate solution for 10 minutes followed by 10 minutes in Reynold's lead citrate. Using a JEOL 1220 80 kV transmission electron microscope, copper grids were thoroughly scanned to locate the emboli of interest.

Human vascular endothelial cell culture and live imaging: (HUVEC) cells were grown on 60 mm Poly D lysine treated glass bottom plates in Medium 200 (Invitrogen). Cells were labeled fluorescently by transduction with an AAV virus driving expression of GFP under a CMV promoter. 24 hours after addition of virus, the culture medium was replaced and cells were grown to confluence. 200 uL of Texas-Red conjugated fibrin clots (5000 clots/mL 8-20 um diameter) were added to the plate and allowed to settle for 15 minutes. The plates were kept at 37C on a heating plate and imaged every 15 minutes for 6 hours using two-photon microscopy.

Statistical analysis: All statistical parameters were calculated using Sigma Plot software. Student's t-test was used for most data analysis. For comparison between more than 2 groups, ANOVA test was used. Mann Whitney test was used for comparing the distribution of relative fluorescence intensities of ZO-1 images. A p value<0.05 was considered to be statistical significance.

Example 2

Enhancement of Microvasculature Occlusion

Experiments were performed during development of embodiments of the present invention to visualize the outcome of individual capillary or terminal arteriole occlusions in the brain. Transcranial imaging in living mice with two photon microscopy (TPM) (Grutzendler et al. Nature 420, 812-6 (2002), herein incorporated by reference in its entirety) as well as high-resolution confocal and electron microscopy were performed after internal carotid infusion of fluorescently conjugated microemboli (8-20 μm). Although a substantial number of these small emboli were cleared after infusion by a combined effect of the fibrinolytic system and hemodynamic forces a large number of emboli remained in the microvasculature and only a modest number of them were washed out thereafter. Thus, although fibrinolysis and hemodynamic forces appear to be relatively effective at early clearance of capillary and microarteriole occlusions, their efficiency is much lower at later stages. Once retained in the microvasculature, emboli generally caused complete cessation of blood flow as demonstrated by the absence of the characteristic pattern of flowing cells observed in TPM line-scan imaging mode.

Figure 2:
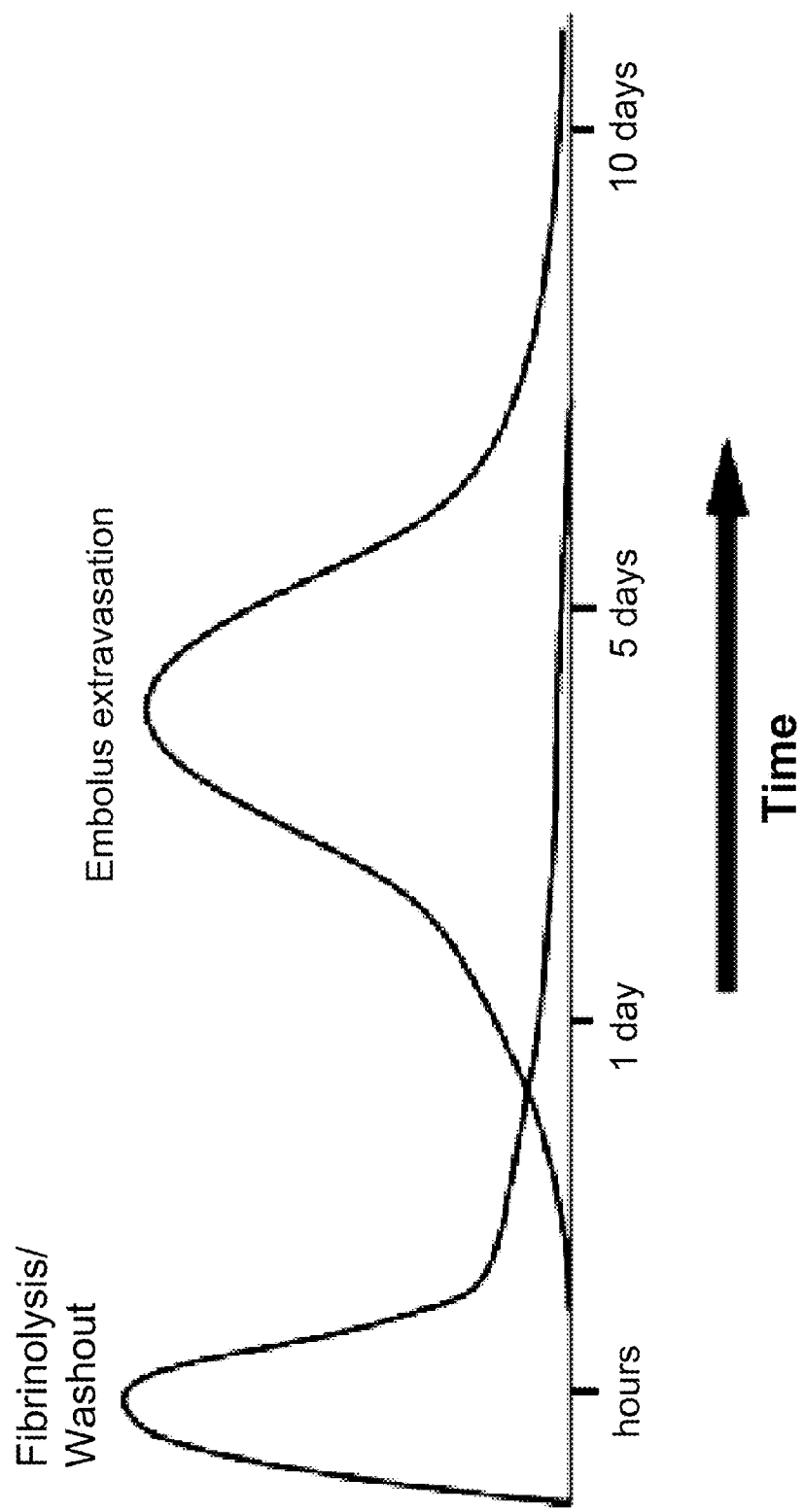
FIG. 2 shows an exemplary time line of the mechanisms of microvascular recanalization: the fibrinolytic system and hemodynamic forces can clear a substantial fraction of emboli (10-20 microns) within the first few hours post embolization. However, once emboli are retained in the microvasculature, these two mechanisms are very ineffective in reestablishing blood flow. Embolus extravasation occurs mostly within the next 2 to 5 days and leads to complete reestablishment of blood flow and sparing of the vessel. In addition, engulfment of smaller embolic fragments that occurs even with emboli that end up being washed out within the first 1-2 days. Thus, partial embolus engulfment and extravasation may occur rapidly after initial occlusion and may contribute to the early washout that is presumed to be solely mediated by fibrinolysis and hemodynamic forces.

Imaging intervals were extended to determine the outcome of persistent vessel occlusions. Unexpectedly, as early as two days post-embolization, many emboli no longer appeared to be located in the interior of the blood vessels and by day 6 the majority of emboli had already translocated outside the vessel lumen completely reestablishing local blood flow. Blood flow was immediately present at the time of imaging in vessels with extravasated blockages, indicating that vessel reflow occurred very rapidly after extravasation was completed. Furthermore, in larger microvessels (~20 µm), which allow the flow of multiple rows of red blood cells, reflow through a partially recanalized area was observed even before complete embolus extravasation (SEE FIG. 2), suggesting that flow reestablishment occurs synchronously with the extravasation process.

Extravasation was observed with fibrin clots as well as with substances not susceptible to fibrinolysis such as cholesterol emboli and polystyrene microspheres. High-resolution in vivo imaging with TPM in mice expressing endothelial-specific GFP (Tie2-GFP) provided a clear demonstration of the extravascular location of emboli. Confocal imaging in fixed tissues immunolabeled for endothelial protein PECAM-1 and extracellular matrix protein collagen IV further confirmed the extravascular location of fibrin, cholesterol and polystyrene emboli. In some cases emboli appeared fully outside and distant from the collagen IV labeled vascular basal lamina while in others they appeared surrounded by basal lamina indicating that a gradual process of extracellular matrix remodeling takes place during and after extravasation. Transmission electron microscopy (TEM) demonstrated fibrin clots and microspheres entirely outside of the patent microvascular lumen and surrounded by processes of a variety of perivascular cells and extracellular matrix. The pattern of clot extravasation was variable with fibrin clots having a tendency to extravasate in smaller fragments (~3-10 µm) though frequently in larger pieces, while cholesterol emboli mostly extravasated as single unfragmented pieces. Thus fragmentation of the occluding material is not essential for extravasation to occur but facilitates the process because smaller emboli tend to extravasate at a faster rate.

Blood vessels retain their normal morphology during the extravasation process as seen by confocal and electron microscopy and in vivo TPM imaging. During the extravasation process, endothelial cells near the occlusion site were not found to express the cell death marker Caspase-3 or the proliferation marker bromodeoxyuridine (BrdU). Therefore, the translocation of emboli does not occur as a result of endothelial cell death but more likely through mechanisms resembling those involved in the passage of inflammatory cells through the blood brain barrier (BBB) or through other as of yet unidentified mechanism (Muller. Trends Immunol 24, 327-34 (2003), Engelhardt & Wolburg. Eur J Immunol 34, 2955-63 (2004), herein incorporated by reference in their entireties), although the present invention is not limited to any particular mechanism of action and an understanding of the mechanism of action is not necessary to practice the present invention.

Single and multiple time point in vivo TPM images were obtained of fibrin and cholesterol emboli as they underwent extravasation through the microvascular endothelium in Tie2-GFP mice to determine the cellular events involved in embolus extravasation. Unexpectedly, regardless of the composition of the embolic material, within 24-48 hours, the endothelium appeared to generate membrane projections that completely enveloped the adjacent embolus. In some cases the new endothelial membrane was in close contact with the opposing endothelium, while in others the two membranes were separate, forming what appeared as a narrow lumen. Sub-cellular imaging with TEM confirmed the presence of the endothelial membrane projection covering entire emboli. Higher magnification TEM showed close contact between the new endothelial membrane and the opposing luminal endothelium. In some cases, vesicular structures were observed, as well as what appeared to be cell-cell adhesion structures resembling adherens junctions between the newly formed and the opposing endothelial membranes (Dejana. Nat Rev Mol Cell Biol 5, 261-70 (2004), herein incorporated by reference in its entirety). In other cases the endothelial membranes looked separate from each other forming a proto-lumen analogous to what was observed by in vivo imaging. The data indicates a sequence of cellular events in which the newly formed endothelial membrane makes transient cell adhesion with the opposing endothelium followed by gradual separation by dissociation of the cellular junctions and possibly by formation of coalescing endothelial vesicles, a mechanism that has been shown to occur during lumen formation in developing blood vessels (Kamei et al. Nature 442, 453-6 (2006), herein incorporated by reference in its entirety). The transient adhesion between the two endothelial membranes may help in the emboli envelopment process and may also serve the purpose of preventing plasma flow from occurring prior to complete envelopment. This would allow the opening of the endothelial barrier for final embolus extrusion while minimizing pathological plasma leakage into the brain parenchyma.

Once emboli are wrapped, their final movement into the parenchyma requires that the original endothelium adjacent to them is disrupted to allow their passage. In vivo imaging in Tie2-GFP mice demonstrated that as the new enveloping membrane is being formed, the original endothelium contacting one side of the embolus undergoes remodeling in what appears to be a retraction process creating a path through which the embolus moves towards the extravascular space. The observed endothelial changes may be due to the formation of a large transcellular channel or paracellular disruption of interendothelial tight junctions, both of which have been proposed as mechanisms of leukocyte transmigration (Muller. Trends Immunol 24, 327-34 (2003), Engelhardt & Wolburg. Eur J Immunol 34, 2955-63 (2004), Carman & Springer. J Cell Biol 167, 377-88 (2004), herein incorporated by reference in their entireties). Confocal images of immunolabeled tight junction (TJ) protein Zonula Occludens-1 (ZO-1) show that ZO-1 labeling intensity is significantly reduced in microvascular areas immediately adjacent to clots as compared to portions of the same vessel distal and proximal to the occlusion site. This suggests that a process of focal TJ disruption may precede endothelial retraction and perivascular basal lamina remodeling prior to final embolus translocation.

In addition to the extravasation of whole emboli, it was observed, especially with fibrin clots, that even as clots were being lysed and washed-out early post embolization, many microvessels retained small fragments from the original clot. Immunolabeling with PECAM-1 and ZO-1 antibodies, which demarcate the microvascular membrane, demonstrated that clot fragments were also enveloped by the membrane of endothelial cells (FIGS. 2p,q) while additional fragments appeared to have extravasated given that they were found outside the membrane boundaries and co-localizing with the collagen IV-labeled basal lamina. Intraendothelial and extravasated clot fragments could be clearly visualized by both confocal and transmission electron microscopy (TEM). Smaller scale engulfment of clot fragments is a phenomenon commonly associated with microvascular occlusion. Given that partial clot engulfment mainly occurs in the first few days after occlusion, in some cases it acts synergistically with hemodynamic forces and the fibrinolytic system to accelerate early clot dislodgment and wash-out.

The process of envelopment and extravasation of emboli is likely to involve complex cellular and molecular events which may include degradation of TJ proteins, adherens junctions and extracellular matrix. Matrix metalloproteinases (MMPs) have been shown to be capable of disrupting these structures and have been implicated in guidance, lumen formation and barrier function in developing blood vessels (Yang et al. J Cereb Blood Flow Metab 27, 697-709 (2007), Stratman et al. Blood 114, 237-47 (2009), herein incorporated by reference in their entireties). The role of MMPs in the extravasation process was investigated by measuring MMP 2/9 activity as reflected by tissue gelatinolytic activity using in situ zymography. Unexpectedly, prominent MMP 2/9 activity was observed specifically in areas immediately adjacent to emboli. This activity may originate from MMPs contained within clots (Kai et al. J Am Coll Cardiol 32, 368-72 (1998), herein incorporated by reference in its entirety) and from adjacent endothelial cells as well as pericytes which undergo hypertrophy near the occlusion site given their increased NG2 expression. To further characterize the role of MMPs in the extravasation process, fibrin clot-embolized mice were treated with the MMP 2/9 inhibitor SB-3CT or saline for 4 days and found a marked reduction in the extravasation of clot fragments in the SB-3CT-treated group. Likewise, SB-3CT administration led to a substantial reduction in microsphere extravasation. Indicating that MMP 2/9 are important in mediating focal proteolytic events at the site of occlusion, and significantly impacting the rate of embolus extravasation.

The impact of microvessel occlusion and recanalization on the structure and viability of blood vessels and surrounding neurons was addressed using microspheres because of their very uniform size and shape. Embolization in 4 month-old mice led to tissue hypoxia as detected by the pimonidazole hydrochloride technique (hypoxyprobe). This hypoxic area was limited to the endothelium and parenchyma generally within ~100 µm of the occlusion site and disappeared following vessel recanalization. At this age, transient hypoxia did not lead to apparent abnormalities of presynaptic structures as detected by immunolabeling of synaptophysin. Minimal perivascular cell death as detected by caspase-3 immunoreactivity or morphological evidence of vascular degeneration was observed after embolization with 15 µm microspheres (but none was detected with 10 µm microspheres). However, quantification of postsynaptic dendritic spines around the occlusion site in mice expressing yellow fluorescent protein (YFP) in neurons demonstrated a significant reduction in spine density which gradually recovered as vessels reestablished blood flow, indicating that sufficient redundancy exists in the cerebral microvasculature that occlusion of a single capillary or precapillary arteriole may only induce sufficient hypoxia to cause local transient synaptic pruning but not cell death.

In contrast, 22 month-old mice showed significantly more persistent hypoxyprobe labeling around the occlusion and frequently developed dystrophic synapses as detected by synaptophysin labeling and a marked increase in caspase-3 immunoreactive perivascular cells. Moreover, comparison of emboli extravasation between young and aged mice demonstrated a remarkably reduced rate in the aged group. Since embolus extravasation is an active process that requires substantial remodeling of the endothelium as well as the extracellular matrix, age-related changes in endothelial cells as well increased basal lamina thickness and collagen deposition may explain the observed reduction in extravasation efficiency (Farkas & Luiten. Prog Neurobiol 64, 575-611 (2001), herein incorporated by reference in its entirety). The increased susceptibility to focal hypoperfusion observed in aging may be explained by a reduced rate of embolus extravasation, coupled with diminished efficiency in compensatory mechanisms to increase regional cerebral blood flow as well as an overall greater cellular vulnerability to hypoxia. Reduced extravasation, may ultimately lead to capillary loss and a decrease in vascular reserve further increasing the susceptibility of the aging brain to microvascular occlusion.

The data describes a previously unknown mechanism of vascular plasticity that leads to recanalization of occluded cerebral capillary and terminal arterioles by extravasation of emboli into the brain parenchyma (SEE FIG. 1). This mechanism is very robust as it almost invariably induces vessel recanalization in situations where fibrinolysis and hemodynamic forces cannot reestablish normal blood flow. Furthermore, this mechanism is likely to be essential for clearing emboli composed of materials such as cholesterol or complex blood clots that are not susceptible to fibrinolysis.

Experiments performed during development of embodiments of the present invention demonstrate that occlusion of terminal arterioles in the cortex, though only affecting the blood flow of a few branches downstream (Nishimura et al. Nat Methods 3, 99-108 (2006), herein incorporated by reference in its entirety), can still cause significant hypoxia and induce transient focal dendritic spine loss in adults as well as more severe synaptic injury and perivascular cell death in aging brains. Therefore, recurrent occlusion of terminal microvessels may have significant pathological consequences, which highlights the potential importance of embolus extravasation in promptly reestablishing vessel patency. This could be of special relevance in aging given that the vasculature may be prone to more frequent or persistent occlusion due to age-related structural vascular changes together with reduced efficiency of the fibrinolytic system (Gleerup Winther. Angiology 46, 715-8 (1995), herein incorporated by reference in its entirety). Furthermore, pathological conditions affecting the microvasculature such as chronic hypertension, diabetes and amyloid angiopathy could further hamper this protective mechanism. Thus, delayed extravasation may not only constitute an independent mechanism of age-related cerebral pathology, but could also contribute to the greater rate of cognitive deterioration in Alzheimer's disease patients in which hypertension and diabetes are co-morbidities (Arvanitakis et al. Arch Neurol 61, 661-6 (2004), Iadecola. Nat Rev Neurosci 5, 347-60 (2004), herein incorporated by reference in their entireties.).

While a normal BBB is essential for maintaining the chemical homeostasis of the brain and abnormalities in the BBB may worsen the outcome of ischemic stroke or lead to neurodegeneration (Abbott et al. Nat Rev Neurosci 7, 41-53 (2006), Zlokovic. Neuron 57, 178-201 (2008), herein incorporated by reference in its entirety), results demonstrate that after microvascular occlusion, a spatially and temporally regulated mechanism of microvascular plasticity leads to a breach in the BBB that serves an important protective role.

Example 3

Inhibition of Recanalization

Figure 3:
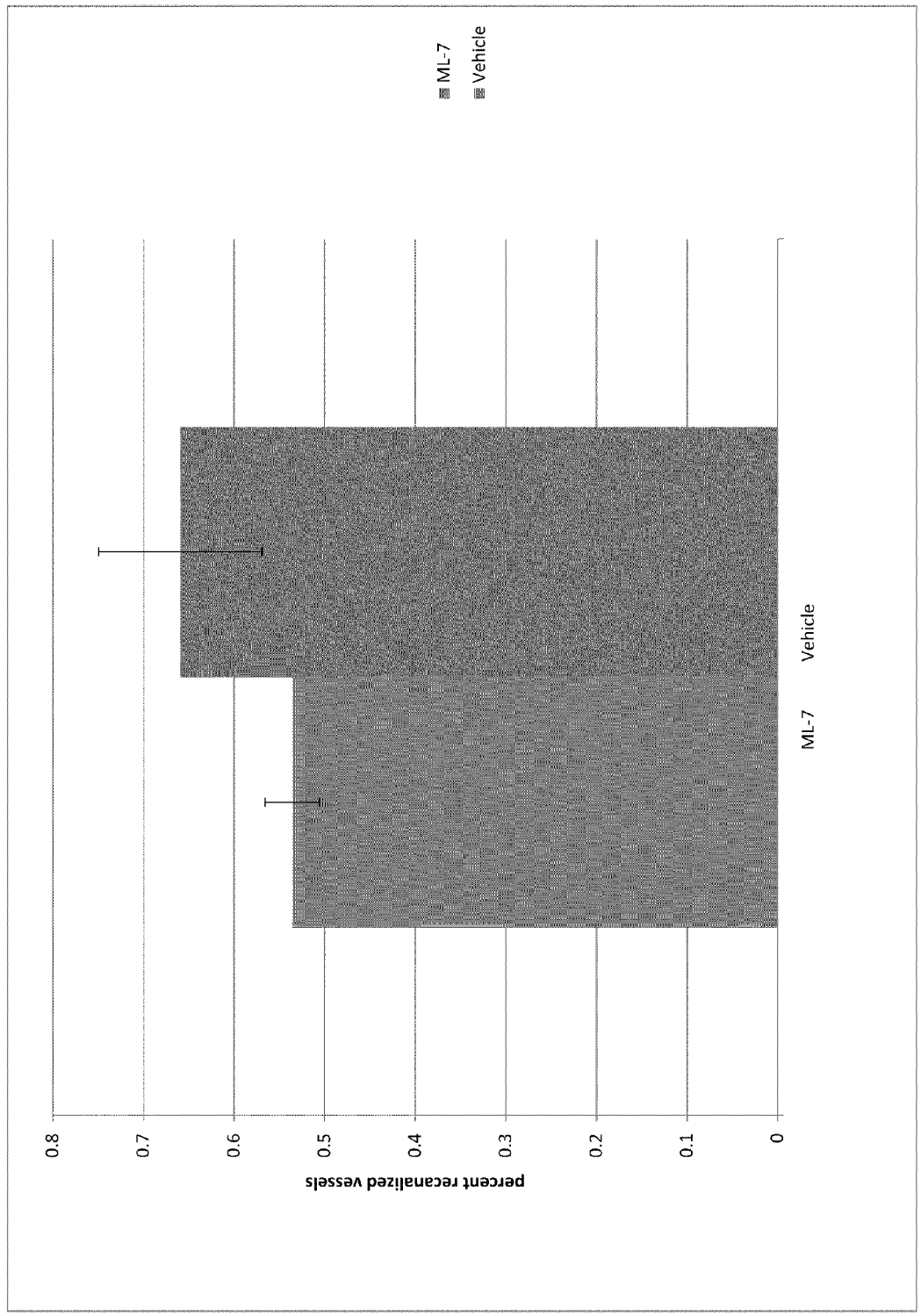
FIG. 3 shows a histogram of recanalization of microvasculature in ML-7 treated and control mice. Mice cerebral vasculatures were embolized by intravascular infusion with either (15 micron microspheres+2 mg/ml ML-7 solution) or (15 micron microspheres+vehicle) followed by daily intraperitoneal injection of ML-7. 14 days later brain tissues were collected and vessels were labeled with fluorescein lectin. The proportion of recanalized occlusions was assessed from 50 randomly selected microsphere in each group.

U87 cancer cells, which model glioma, were implanted in mice to create a tumor. Tumors were embolized by intravascular infusion with either (15 micron microspheres+2 mg/ml ML-7 solution) or (15 micron microspheres+vehicle). 7 days later brain tissues were collected and vessels were labeled with anti CD 31 antibodies. Cell death marker caspase 3 was labeled with anti caspase 3 antibody. Without ML-7 to inhibit extravasation of emboli, individual emboli cause a moderate amount of caspase upregulation and tumor blood vessels are recanalized re-establishing blood flow to the tumor. ML-7 treated microspheres caused a broad upregulation of cell death marker Caspase-3 within the cancer. The proportion of recanalized occlusions was assessed for each group. ML-7 treated mice showed less extravasated emboli, and fewer of occluded vessels had been re-canalized (SEE FIG. 3).

REFERENCES

The references cited herein throughout, to the extent that they provide exemplary procedural or other details supplementary to those set forth herein, are all specifically incorporated herein by reference. The following references are also incorporated by reference in their entireties:

Abbott et al. (2006) Nat Rev Neurosci 7:41-53.
Arvanitakis et al. (2004) Arch Neurol61:661-666.
Busch et al. (1998) J Cereb Blood Flow Metab 18:407-418.
Caplan & Hennerici (1998) Arch Neurol55:1475-1482.
Collen (1980) Thromb Haemost 43:77-89.
Davies (1995) Physiol Rev 75:519-560.
Dermietzel et al. (2006) Blood-brain barriers: from ontogeny to artificial interfaces. Weinheim; [Chichester]: Wiley-VCH.
Farkas & Luiten (2001). Prog Neurobiol64:575-611.
Gleerup & Winther (1995) Angiology 46:715-718.
Ladecola & Gorelick (2003) Stroke 34:335-337.
Kai et al. (1998) JAm Coli Cardiol32:368-372.
Levin & del Zoppo (1994) Am J Pathol144:855-861.
Lo et al. (2004) Stroke 35:354356.
Mark & Davis (2002) Am J Physiol Heart Circ Physiol 282: H1485-1494.
Markus et al. (1995) Brain 118 {Pt 4):1005-1011.
Muller (2003) Trends Immunol24:327-334.
Peppiatt et al. (2006) Nature 443:700-704.
Powers et al. (1985) J Cereb Blood Flow Metab 5:600-608.
Pugsiey et al. (1994) Stroke 25:1393-1399.
Purandare et al. (2007) Bioi Psychiatry 62:339-344.
Rapp et al. (2000) J Vasc Surg 32:68-76.
Rieckmann & Engelhardt (2003) Nat Med 9:828-829.
Siebler et al. (1994) Neurology 44:615618.
Vermeer et al. (2003) N Engl J Med 348:1215-1222.
Wagner & Chen (1991) Microvasc Res 42:139-150.
Yong et al. (2001) Nat Rev Neurosci 2:502-511.
Zhao et al. (2006) Nat Med 12:441-445.
Ziokovic (2008) Neuron 57:178-201.

We claim:

1. A method of occluding blood flow to a tumor of a subject comprising:
    (a) administering a first composition comprising synthetic microspheres to microvasculature within said tumor; and
    (b) administering a second composition comprising a MMP 2/9 inhibitor to said tumor;
wherein steps (a) and (b) result in a least partial occlusion of blood flow to said tumor in said subject.

2. The method of claim 1, wherein said MMP 2/9 inhibitor is selected from SB-3CT and ML-7.

3. The method of claim 1, wherein said synthetic microspheres are 5-20 μm in diameter.

4. The method of claim 3, wherein said synthetic microspheres comprise polystyrene, chitosan, agarose, and/or gelatin.

5. The method of claim 1, wherein step (a) is performed prior to step (b).

6. The method of claim 1, wherein step (b) is performed prior to step (a).

7. The method of claim 1, wherein said synthetic microspheres do not carry a cargo comprising said MMP 2/9 inhibitor.

* * * * *